United States Patent [19]

Fujisawa

[11] Patent Number: 5,087,659
[45] Date of Patent: Feb. 11, 1992

[54] INK COMPOSITIONS AS STEAM STERILIZING INDICATORS FOR USE IN INK JET PRINTING

[75] Inventor: Toshiki Fujisawa, Osaka, Japan

[73] Assignee: Sakura Color Products Corporation, Osaka, Japan

[21] Appl. No.: 416,324

[22] Filed: Oct. 2, 1989

[30] Foreign Application Priority Data

Sep. 30, 1988 [JP] Japan .................................. 63-248529

[51] Int. Cl.$^5$ ............................................. C08L 61/10
[52] U.S. Cl. .................................... 524/594; 525/502; 422/26
[58] Field of Search ......................... 524/594; 525/502; 422/26

[56] References Cited

U.S. PATENT DOCUMENTS 4,465,800  8/1984  Bhatia ................................. 524/236
4,605,441  8/1986  Masuda et al. ........................ 106/21

Primary Examiner—Maurice J. Welsh
Assistant Examiner—Rachel Johnson
Attorney, Agent, or Firm—Wenderoth, Lind & Ponack

[57] ABSTRACT

An ink composition as a steam sterilizing indicator for use in ink jet printing which comprises a salt of a cyanine dyestuff with phenol resins in amounts of 0.1-5% by weight as the cyanine dyestuff and in amounts of 0.2-30% by weight as the phenol resins, dissolved in organic solvents in amounts of 70-96% by weight based on the ink composition.

The ink composition may further contain at least one of alkali metal salts, resins containing carboxyl groups therein, aliphatic carboxylic acids, anticorrosion agents, nonionic surfactants and dyestuffs which are unchanged in color under sterilizing conditions.

The ink composition is discolored or changes in color under steam sterilization conditions.

11 Claims, No Drawings

INK COMPOSITIONS AS STEAM STERILIZING INDICATORS FOR USE IN INK JET PRINTING

This invention relates to an ink composition as a steam sterilizing indicator for use in ink jet printing, and more particularly, to an ink composition applied on the surface of substrates such as food and beverage cans in ink jet printing operations to indicate the completion or extent of sterilization of the substrates in steam sterilization in autoclaves. The invention further relates to a method of producing the above ink composition as a steam sterilizing indicator for use in ink jet printing and a method of steam sterilization of substrates using the above ink composition as a sterilizing indicator.

During the production steps of food or beverage cans such as coffee, lot numbers or date of production are printed in ink jet printing operations on the tops or bottoms of the metal cans with ink compositions, and the cans are placed in a steam sterilizers such as autoclaves to steam sterilize the products in the cans under high temperature and high moisture conditions. However, usually since a large number of cans are placed in autoclaves in such sterilization, it often happens that not all the cans are sufficiently heated for a sufficient period of time.

There has been proposed a test paper which is used as a sterilizing indicator in the sterilization of operation instruments, for example, in Japanese Patent Publication No. 52-2324 and Japanese Patent Laid-open No. 61-123682. The test paper has chemical compositions coated thereon which change color depending upon temperature, and is used in such a manner that it is placed in sterilizers together with operation instruments to indicate whether the temperature is sufficiently high for the sterilization. However, it is not realistic to apply the test paper to each of a great number of cans before the sterilization operation and separate it from the cans after the sterilization operation.

Therefore, there has been proposed in Japanese Patent Publication No. 62-9148 an ink composition for use in ink jet printing which is changeable in color when exposed to high temperature steam. The ink composition is composed of an aliphatic alcohol and a combination of a dyestuff which is extractable with water and a dyestuff which is not extractable with water both dissolved therein together with resol resins. The ink composition therefore changes color when it is heated under high temperature and high moisture conditions since the water-extractable dyestuff is extracted with water. However, the ink composition has a drawback derived from the inclusion of the water-extractable dyestuff to make the ink composition color-changeable when heated in the presence of moisture. Namely, the ink composition provides printing which is inferior in water resistance and readily gets blurred before the exposure to steam, but also the change in color is not clear when exposed to steam, to render the printing blurred.

It is, therefore, an object of the invention to provide an ink composition as a steam sterilizing indicator for use in jet ink printing which contains a discolorable or color-changeable colorants when exposed to high temperature and high moisture, so that it provides water-resistant and clear printing on substrates during steam sterilizing operations.

The ink composition of the invention as a steam sterilizing indicator for use in ink jet printing comprises a salt of a cyanine dyestuff with phenol resins in amounts of 0.1-5% by weight as the cyanine dyestuff and in amounts of 0.2-30% by weight as the phenol resins, dissolved in organic solvents in amounts of 70-96% by weight based on the ink composition.

The organic solvents used include, for example, aliphatic alcohols such as methanol, ethanol, propanol or butanol, alicyclic alcohols such as cyclohexanol, alkylene glycol monoalkylethers such as ethylene glycol monomethyl ether, ethylene glycol monoethyl ether, ethylene glycol monobuhyl ether or propylene glycol monomethyl ether, alkyleneglycol monoesters such as ethylene glycol monoacetate, and ketones such as methyl ethyl ketone, methyl isobutyl ketone, isophorone or cyclohexanone. These solvents may be used singly or as a mixture of two or more.

When the amount of the solvent is too large, the resultant ink composition is inferior in adhesion or insufficient in darkness of printing, whereas when the amount of the solvent is too small, the resultant ink composition is too viscous to use in ink jet printing operations. Thus, the ink composition of the invention contains the solvent usually in amounts of 70-96% by weight, preferably in amounts of 75-92% by weight.

The dyestuff used is a cyanine dyestuff which has formed a salt with phenol resins. The cyanine dyestuff has the general formula:

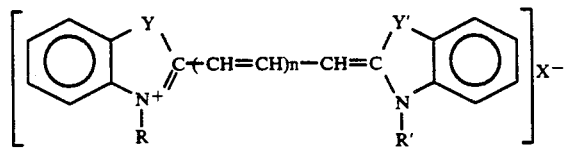

wherein Y and Y' represent O, S, Se, NH, CH=CH and the like; R and R' represent alkyl groups; X represents halogen atoms; and n is integers of 0-3, and has quaternary ammonium steuctures, as described in Encyclopaedia Chimica, Vol. 4, P. 26 (1977), Kyoritsu Shuppan K.K., Tokyo.

The cyanine dyestuffs used in the invention are not specifically limited, but include, for example, C.I. Basic Red 12, 13, 14, 15, 27, 35, 36, 37, 45, 48, 49, 52, 53, 66 and 68. These may be used singly or as a mixture of two or more.

The salt of a cyanine dyestuff with phenol resins used in the ink composition of the invention is obtained as solids by dissolving a cyanine dyestuff and a phenol resin in an lower aliphatic alcohol, heating the resultant mixture and then removing the alcohol by distillation. Herein the specification, the thus obtained solids are called the salt of a cyanine dyestuff with phenol resins and abbreviated to the cyanine salt. As the above mentioned alcohol as the solvent, methanol, ethanol or isopropanol may be used, and the first two or a mixture thereof are preferred.

A variety of phenol resins may be used to form the cyanine salts, for example, phenol resins, alkylphenol resins or rosin modified phenol resins. The phenol resins may be resols or novolaks, and may be readily available as, for example, Tamanol 100S by Arakawa Kagaku Kogyo K.K. or Hitanol 1501 by Hitachi Kasei Kogyo K.K.

In the production of the cyanine salts, the phenol resins are used in amounts of 2-15 times, preferably in amounts of 3-10 times, most preferably in amounts of 5-8 times, in weight as much as the amount of the cyanine dyestuff used. It is enough that the solvent is used in such a manner that it dissolves the cyanine dyestuff and the phenol resins used therein. Usually the solvent is used in amounts of 1–5 times in weight as much as the phenol resins used.

The cyanine salt is completely discolored or gets colorless when being heated under high temperature and high moisture conditions, and in addition, it provides printing on substrates such as metal cans which is highly water resistant so that it does not get blurred during the steam sterilizing operations. The printing is also very adhesive to the substrates.

The cyanine salt is contained in the ink composition in amounts, as cyanine dyestuffs, of 0.1–5% by weight, preferably of 0.5–3% by weight, based on the ink composition. When the amount of the cyanine salt is less than 0.1% by weight as cyanine dyestuffs based on the ink composition, the resultant printing is insufficient in darkness, and fails to indicate clear discoloration in sterilizing operations. On the other hand, when the amount of the cyanine salt is more than 5% by weight as cyanine dyestuffs based on the ink composition, the resultant printing is not completely discolored.

Further, the cyanine salt is contained in amounts, as phenol resins, of 0.2–30% by weight, preferably in amounts of 1–20% by weight, and most preferably in amounts of 3–15% by weight, based on the ink composition. When the amount of the cyanine salt is less than 0.2% by weight as phenol resins based on the ink composition, the resultant printing is still insufficient in water resistance, and may get blurred during sterilizing operations. Further, the printing may not completely discolored during sterilizing operations. On the other hand, when the amount of the cyanine salt is more than 20% by weight as phenol resins based on the ink composition, the resultant ink composition is not suitable for use in ink jet printing on account of its excessivly high viscosity. The ink composition may contain free phenol resins, if desired.

In accordance with the invention, there is provided an ink composition further containing a second dyestuff which is not color-changeable or remains unchanged in color under high temperature and high moisture conditions. This ink composition containing such a second dyestuff changes color during sterilizing conditions since the cyanine salt is discolored or gets colorless while the second dyestuff remains the same in color. The second dyestuff usable is not specifically limited, as will be apparent, provided that it is soluble in the solvents used. However, from practical standpoint, it is preferred that the second dyestuff is selected in consideration of color before the heating of the printing of the ink composition, namely the color as a mixture with the cyanine salt used and color after the heating of the printing, namely the color of the second dyestuff itself. The amount of the second dyestuff is also selected in the same manner as above described.

The ink composition of the invention may further contain a resin which has carboxyl groups therein to improve adhesion of the ink compositions to substrates or to control the degree of discoloration or change in color. Such resins used include, for example, rosin, hydrogenated rosin, rosin ester, rosin modified maleic resin or rosin modified phenol resin. These resins are readily available as commercial products. For example, rosin is available as Rosin H by Tokushima Seiyu K.K. Maleic resins or styrene-maleic copolymer resins may be also preferably used as second resins. Maleic resins are available as, for example, Teskyd MRA, MRM-11, MRM-42 or MRM-53 by Tokushima Seiyu K.K., or Malkyd 33 by Arakawa Kagaku Kogyo K.K., and styrene-maleic copolymer resins as, for example, Suprapal AP20 or AP30 by BASF.

The carboxyl group containing resins may be contained in amounts of not more than 20% by weight, preferably in amounts of not more 15% by weight, based on the ink composition. When the resin is contained in excessive amounts, the resulting ink composition is not suitable for use in ink jet printing on account of its excessively high viscosity.

It is preferred that the ink composition contain a salt of alkali metals to increase electroconductivity of the ink composition. The alkali metal salts used include inorganic salts such as alkali metal halides, e.g., lithium bromide, potassium bromide, lithium chloride, sodium chloride, potassium chloride, lithium iodide, potassium iodide or sodium iodide, and organic carboxylates such as sodium acetate, sodium propionate, potassium butyrate, sodium oleate, sodium benzoate, sodium palmitate or sodium stearate, among which are preferred lithium chloride or sodium acetate.

It is preferred that the ink composition contain a salt of alkali metals in amounts of not more than 8% by weight, preferably in the range of 0.2–8% by weight, most preferably in amounts of 0.5–5% by weight, based on the ink composition so that the ink composition has an electroconductivity suitable for use in ink jet printing. It is not desired to use the salts in excessive amounts since portions of the salts remain undissolved in the solvents so that the ink composition deteriorates in ink jet printability, but also the ink composition gets corrosive to metals.

The ink composition of the invention may further contain an aliphatic carboxylic acid. In particular, it is preferred that the ink composition contain such an aliphatic carboxylic acid in amounts of not more than 5% by weight based on the ink composition together with the above mentioned alkali metal salts to prevent the printing from undesired change in color when the printing is left standing at room temperatures. Acetic acid is preferred for the purpose, but higher aliphatic carboxylic acids such as propionic acid, butyric acid or valeric acid may be used, if necessary.

Anticorrosion agents may be contained in effective amounts in the ink composition of the invention to prevent the corrosion of metal parts of nozzles in ink jet printers or metal substrates on which printing is made. The amount of anticorrosion agents may usually be 0.5–6% by weight, preferably 1–4% by weight, based on the ink composition. The use of excessive amounts of anticorrosion agents makes printability of the ink composition bad.

There may be mentioned as such anticorrosion agents, for example, organic acids or their metal salts such as dodecylsuccinic acid, malonic acid or hydroxyphenylstearic acid, metal soaps such as aluminum stearate, magnesium palmitate or cobalt naphthenate, tertiary alcohols containing acetylenic bonds therein such as methylpentynol or hexynol, phenols such di-t-butylphenol, phosphates such as ethyl phosphate, tributyl phosphate, sulfonic acids, alkali metal sulfonates, amine sulfonates or sulfonamides including petroleum sulfonic acid, amines such as diethylamine or phenylnaphthylamine, acid amides such as stearoyl amide, and mercaptans such as mercaptobenzothiazole or its condensates with polyethylene glycol. There may also be used lanoline or eugenol as anticorrosion agents. These anticorrosion agents may be used singly or as a mixture of two or more.

The ink composition of the invention may be applied by jet ink printing manners to substrates including paper materials such as retort bags, glass materials such as glass bottles for antiseptic solutions, metal materials such as metal cans for foods or beverages, synthetic films, metal foils or laminates thereof for retort pouches. The metal substrates may have resin or oily coatings thereon.

There may be further contained nonionic surfactants in effective amounts in the ink composition of the invention to assure clear and adhesive printing on substrates which have film of paraffin or grease thereon which usually repels the ink composition. Such nonionic surfactants usable include, for example, ether surfactants such as alkylpolyoxyethylene ether, alkylarylpolyoxyethylene ether, glycerine ether or alkylthiopolyoxyethylene ether, ester/ether surfactants such as polyoxyethylene ether of propylene glycol ester or sorbitan ester, ester surfactants such as polyoxyethylene fatty acid ester, sorbitan ester or sucrose ester, nitrogen containing surfactants such as fatty acid alkanolamide, alkanolamine ester or amine oxides, and in addition, fluorinated, silicone or polypeptide surfactants.

The nonionic surfactants may be contained in amounts usually of 0.1-5% by weight, preferably in amounts of 0.5-3% by weight, based on the ink composition. When the amount of the nonionic surfactants is less than 0.1% by weight based on the ink composition, the ink composition is repelled by the film when ink jet printed on the surface of the substrates having film of paraffin or grease, whereas when the amount is more than 5% by weight, the ink composition is too large in resistivity and unstable in ink jet printability.

The ink composition of the invention may be produced by any method known in the art. By way of example only, the cyanine salt is placed in a vessel together with organic solvents and additives, and then dissolved in the solvents under stirring at room temperatures or, if necessary, at elevated temperatures such as 70° C. Then the mixture is cooled and, if necessary solid components are removed by filtration preferably with a membrane filter having micropores of about 0.5 μm in diameter.

As set forth about, the ink composition of the invention contain the cyanine salt with phenol resins as colorants, and can be applied onto substrates by an ink jet printing manner without getting blurred and with good adhesion. Furthermore, the printing with the ink composition is completely discolored, or clearly changes in color when containing a second dyestuff as previously described, under sterilizing conditions, without getting blurred, thereby to clearly indicate the completion or extent of sterilization of the products in the substrates.

The invention will now be described with reference to examples, however, the examples are illustrative only, and the invention is not limited thereto. Parts are parts by weight.

EXAMPLE 1

The following mixture was prepared and boiled under heating to remove all the ethanol by distillation, to provide a cyanine salt.

| | |
|---|---|
| SWT-Red 4 (C.I. Basic Red 14 by Hodogaya Kagaku Kogyo K.K.) | 1.5 parts |
| Tamanol 100S (alkylphenol resins by Arakawa Kagaku Kogyo K.K.) | 10.0 parts |
| Ethanol | 30.0 parts |

Then the following ink composition was prepared. The ink composition had a resistivity of 1400 Ω.cm at 25° C. The ink composition provided clear red printing on cans in ink jet printing. The cans were steam-heated at 121° C. under 1 Kg/cm² over 20 minutes to make the printing colorless.

| | |
|---|---|
| Cyanine salt | 11.5 parts |
| Ethanol | 68.5 parts |
| Ethylene glycol monoethyl ether | 20.0 parts |

EXAMPLE 2

The following mixture was boiled under heating to remove all the methanol by distillation to provide a cyanine salt.

| | |
|---|---|
| Aizen Cathilon Brilliant Scarlet RH Conc (C.I. Basic Red 37 by Hodogaya Kagaku Kogyo K.K.) | 1.0 part |
| Hitanol 1501 (alkylphenol resins by Hitachi Kasei Kogyo K.K.) | 5.0 parts |
| Methanol | 15.0 parts |

Then the following ink composition was prepared using the cyanine salt. The ink composition had a resistivity of 900 Ω.cm at 25° C. The ink composition provided clear violet printing on glass bottles in ink jet printing. The bottles were steam-heated at 121° C. under 1 Kg/cm² over 20 minutes. The printing was found clear blue.

| | |
|---|---|
| Cyanine salt | 6.0 parts |
| Oil Blue #8 (derivative of Basic Blue 7 by Chuo Gosei Kagaku K.K.) | 0.8 parts |
| Hypale (Hydrogenated rosin by Arakawa Kagaku Kogyo K.K.) | 0.6 parts |
| Lithium chloride | 1.0 part |
| Cyclohexanone | 25.0 parts |
| Methanol | 31.2 parts |
| Ethylene glycol monoethylether | 22.0 parts |
| Ethylene glycol monobutylether | 8.0 parts |

EXAMPLE 3

The following mixture was boiled under heating to remove all the isopropanol by distillation to provide a cyanine salt.

| | |
|---|---|
| Aizen Brilliant Pink PGH 200% (C.I. Basic Red 27 by Hodogaya Kagaku Kogyo K.K.) | 1.0 parts |
| Hitanol 1133 (alkylphenol resins by Hitachi Kasei Kogyo K.K.) | 7.0 parts |
| Isopropanol | 14.0 parts |

The following ink composition was prepared using the cyanine salt. The ink composition had a resistivity of 1500 Ω.cm at 25° C. Clear red images were printed on the surface of a retort pouch composed of laminates of polyamide/aluminum foil polyolefin with the ink composition in ink jet printing. The retort pouch was steam-heated at 121° C. under 1 Kg/cm² over 20 minutes. The images were disclored and disappeared.

| Cyanine salt | 8.0 parts |
|---|---|
| Suprapal AP 30 (styrene-maleic resin by BASF) | 3.0 parts |
| Tespol 1150 (rosin-modified maleic resin by Hitachi Kasei Kogyo K.K.) | 2.0 parts |
| Sodium acetate | 4.0 parts |
| Isopropanol | 52.0 parts |
| Propylene glycol monomethyl ether | 25.0 parts |
| Ethylene glycol monobutyl ether | 5.0 parts |
| Stearoyl amide | 1.0 parts |

EXAMPLE 4

The following mixture was prepared and boiled under heating to remove all the ethanol by distillation to provide a cyanine salt.

| Aizen Cathilon Brilliant Pink BH (C.I. Basic Red 36 by Hodogaya Kagaku Kogyo K.K.) | 2.0 parts |
|---|---|
| Tamanol 510 (alkylphenol resins by Arakawa Kagaku Kogyo K.K.) | 12.0 parts |
| Ethanol | 36.0 parts |

The following ink composition was prepared using the cyanine salt. The ink composition had a resistivity of 900 Ω.cm at 25° C. Clear red images were printed on the surface of bleached kraft paper for retort bags with the ink composition in ink jet printing. The paper was steam-heated at 121° C. under 1 Kg/cm² over 20 minutes. The images were discolored and disappeared.

| Cyanine salt | 14.0 parts |
|---|---|
| Lithium chloride | 1.0 parts |
| Cyclohexanone | 10.0 parts |
| Ethanol | 42.0 parts |
| Ethylene glycol monoethyl ether | 30.0 parts |
| Silicone surfactant | 3.0 parts |

COMPARATIVE EXAMPLE 1

The solution of the following mixture was prepared. The resultant ink composition had a resistivity of 1400 Ω.cm at 25° C. Red printing was formed on cans with the ink composition in ink jet printing. But after steam-heating at 121° C. for 20 minutes, the printing was found not to be completely discolored, but was found to change in color to pale red.

| SWT-Red 4 (C.I. Basic Red 14 by Hodogaya Kagaku Kogyo K.K.) | 1.5 parts |
|---|---|
| Tamanol 100S (alkylphenol resin by Arakawa Kagaku Kogyo K.K.) | 10.0 parts |
| Ethanol | 68.5 parts |
| Ethylene glycol monoethyl ether | 20.0 parts |

COMPARATIVE EXAMPLE 2

The solution of the following mixture was prepared. The resultant ink composition had a resistivity of 900 Ω.cm at 25° C. There were printed violet images on glass bottles with the resultant ink composition in ink jet printing. But the images were found to change in color to blue tinged with red after steam-heating at 121° C. for 20 minutes.

| Aizen Cathilon Brilliant Scarlet RH Conc (C.I. Basic Red 37 by Hodogaya Kagaku Kogyo K.K.) | 1.0 part |
|---|---|
| Oil Blue #8 (derivative of Basic Blue 7 by Chuo Gosei Kagaku K.K. | 0.8 parts |
| Hitanol 1501 (alkylphenol resins by Hitachi Kasei Kogyo K.K.) | 5.0 parts |
| Cyclohexanone | 25.0 parts |
| Methanol | 31.2 parts |
| Ethylene glycol monoethyl ether | 22.0 parts |
| Ethylene glycol monobutyl ether | 8.0 parts |

COMPARATIVE EXAMPLE 3

The solution of the following mixture was prepared. The resultant ink composition had a resistivity of 1500 Ω.cm at 25° C. There were printed red images on the surface of a retort pouch composed of laminates of polyamide/aluminum foil polyolefin with the ink composition in ink jet printing. The retort pouch was steam-heated at 12° C. under 1 Kg/cm² over 20 minutes. The images were found not completely discolored, but were found to change in color to pale red.

| Aizen Brilliant Pink BGH 200% (C.I. Basic Red 27 by Hodogaya Kagaku Kogyo K.K.) | 1.0 part |
|---|---|
| Hitanol 1133 (alkylphenol resins by Hitachi Kasei Kogyo K.K.) | 7.0 parts |
| Suprapal AP 30 (styrene-maleic resin by BASF) | 3.0 parts |
| Tespol 1150 (rosin-modified maleic resin by Hitachi Kasei Kogyo K.K.) | 2.0 parts |
| Sodium acetate | 4.0 parts |
| Isopropanol | 52.0 parts |
| Propylene glycol monomethyl ether | 25.0 parts |
| Ethylene glycol monobutyl ether | 5.0 parts |

COMPARATIVE EXAMPLE 4

The solution of the following mixture was prepared. The resultant ink composition had a resistivity of 900 Ω.cm at 25° C. There were printed red images on bleached kraft paper for retort bags with the ink composition in ink jet printing. The paper was steam-heated at 121° C. under 1 Kg/cm² over 20 minutes. The images were found not completely discolored and disappeared, but were found to change in color to pale red.

| Aizen Cathilon Brilliant Pink BH (C.I. Basic Red 36 by Hodogaya Kagaku Kogyo K.K.) | 2.0 parts |
|---|---|
| Tamanol 510 (alkylphenol resins by Arakawa Kagaku Kogyo K.K.) | 12.0 parts |
| Lithium chloride | 1.0 parts |
| Cyclohexanone | 10.0 parts |
| Ethanol | 42.0 parts |
| Ethylene glycol monoethyl ether | 30.0 parts |
| Silicone surfactant | 3.0 parts |

EXAMPLE 5

Color difference (ΔE) before and after the steam-heating of the ink compositions of the Examples 1–4 and the Comparative Examples 1–4 was measured with a color difference meter. The results are shown in the Table 1.

The red ink compositions of the Examples 1, 3 and 4 were completely discolored and became colorless after the steam-heating while the red ink composition of the Example 2 changed in color to clear blue. Thus, their color differences are large. On the contrary, the ink compositions of the Comparative Examples 1–4 have small color differences on account of insufficient discoloration of the cyanine dyestuffs used.

TABLE 1

| Ink Compositions | ΔE |
|---|---|
| Example 1 | 47.9 |
| Example 2 | 38.6 |
| Example 3 | 40.3 |
| Example 4 | 41.5 |
| Comparative 1 | 19.7 |
| Comparative 2 | 15.2 |
| Comparative 3 | 17.8 |
| Comparative 4 | 18.0 |

EXAMPLE 6

This Example is to illustrate high water resistance of the ink composition of the invention.

An amount of 5 g of the cyanine salt a was added to 100 g of water and stirred at 40° C. Insoluble solids were removed from the mixture by filtration with a No. 1 filter paper. Based on the measurement of weight of the insoluble solids, the cyanine salt was found to have a solubility of 0.08 g/100 ml of water.

For comparison, 1.5 parts of SWT-Red 4 (C.I. Basic Red 14 by Hodogaya Kagaku Kogyo K.K.) and 10.0 parts of Tamanol (alkylphenol resin by Arakawa Kagaku Kogyo K.K.) were added to 30.0 parts of ethanol, and stirred at 40° C. over one hour. The mixture was filtered to remove insoluble solids with a No. 1 filter paper, and then ethanol was removed from the filtrate by distillation under reduced pressures, to provide a solid dyestuff b.

An amount of 5 g of the solid dyestuff was added to 100 g of water and stirred at 40° C. Insoluble solids were removed from the mixture by filtration with a No. 1 filter paper. Based on the measurement of weight of the insoluble solids, the solid dyestuff was found to have a solubility of 0.90 g/100 ml of water.

Thus it is illustrated that the cyanine salt is excellent in water resistance. Similar results were obtained with the cyanine salts prepared using methanol or isopropanol.

EXAMPLE 7

This Example is to illustrate discoloring properties of the ink compositions upon exposure to high temperature and high moisture conditions.

An amount of 11.5 g of the cyanine salt prepared in the Example 6 were added to 68.5 parts of ethanol and 20.0 parts of ethylene glycol monoethyl ether to provide an ink composition A. Similarly, an ink composition B was prepared in the same manner as above except the use of 11.5 g of the solid dyestuff prepared in the Example 6 in place of the cyanine salt.

For comparison, the following two ink compositions were prepared.

An amount of 10.0 parts of Tamanol 100S (alkylphenol resin by Arakawa Kagaku Kogyo K.K.) was dissolved in 68.5 parts of ethanol, and then there were added thereto 1.5 parts of SWT-Red 4 (C.I. Basic Red 14 by Hodogaya Kagaku Kogyo K.K.). The resulting mixture was refluxed over a period of one hour to prepare a dyestuff solution. An amount of 20.0 parts of ethylene glycol monoethyl ether was added to the dyestuff solution, and stirred. The resultant mixture was filtered with a membrane filter having micropores of 0.5 μm, to prepare an ink composition C.

A mixture of 1.5 parts of SWT-Red 4, 10.0 parts of Tamanol 100S, 3 parts of ethanol and 20.0 parts of ethylene glycol monoethyl ether were heated at 70° C. under stirring, cooled, and then filtered with a membrane filter having micropores of 0.5 μm, to provide an ink composition D.

The individual ink compositions thus prepared were coated in a thickness of 20 μm on tin coated steel plates with a bar coater and heated with steam at 121° C. in an autoclave over 20 minutes. The color difference of the ink composition before and after the sterilizing heating conditions are shown in the Table 2.

TABLE 2

| Ink Compositions | ΔE |
|---|---|
| A | 47.9 |
| B | 20.6 |
| C | 21.2 |
| D | 19.7 |

The ink composition A of the invention, originally red, was completely discolored or became colorless after the heating, whereas the ink compositions B to D were not completely discolored but were found pale red, so that the compositions B to D had small color differences before and after the heating.

What is claimed is:

1. An ink composition as a steam sterilizing indicator for use in ink jet printing which comprises a salt of a cyanine dyestuff with phenol resins in amounts of 0.1–5% by weight as the cyanine dyestuff and in amounts of 0.2–30% by weight as the phenol resins, dissolved in organic solvent in amounts of 70–96% by weight of solvent based on the ink composition.

2. The ink composition as claimed in claim 1 which further contains an alkali metal salt in amounts of not more than 8% by weight based on the ink composition.

3. The ink composition as claimed in claim 1 which further contains a resin containing carboxyl groups therein selected from the group consisting of rosin, hydrogenated rosin, rosin ester, rosin-modified phenol resin, maleic resin and styrene-maleic copolymer resin, in amounts of not more than 20% by weight based on the ink composition.

4. The ink composition as claimed in claim 1 which further contains an aliphatic carboxylic acid in amounts of not more than 5% by weight based on the ink composition.

5. The ink composition as claimed in claim 1 which further contains an anticorrosion agent in effective amounts.

6. The ink composition as claimed in claim 1 which further contains a nonionic surfactant in effective amounts.

7. The ink composition as claimed in claim 1 which further contains a dyestuff which is unchanged in color under sterilizing conditions.

8. A method of producing an ink composition as a steam sterilizing indicator for use in ink jet printing which comprises dissolving a cyanine dyestuff and a phenol resin in lower aliphatic alcohols and heating the mixture to remove the alcohols to provide a salt of the cyanine dyestuff with the phenol resin, and dissolving the salt in organic solvents.

9. The method as claimed in claim 8 wherein the alcohol is selected from the group consisting of methanol, ethanol and isopropanol.

10. A method of steam sterilization of substrates which comprises applying an ink composition as a steam sterilizing indicator on the substrates in ink jet printing operations, the ink composition comprising a salt of a cyanine dyestuff with phenol resins in amounts of 0.1–5% by weight as the cyanine dyestuff and in amounts of 0.2–30% by weight as the phenol resins, dissolved in organic solvent in amounts of 70–96% by weight of solvent based on the ink composition.

11. The method as claimed in claim 10 wherein the ink composition further contains at least one of alkali metal salts, resins containing carboxyl groups therein selected from the group consisting of rosin, hydrogenated rosin, rosin ester, rosin-modified phenol resin, maleic resin and styrene-maleic copolymer resin, aliphatic carboxylic acids, anticorrosion agents, nonionic surfactants and dyestuffs which are unchanged in color under sterilizing conditions.

* * * * *